United States Patent
Dollings

(12) 
(10) Patent No.: US 6,187,755 B1
(45) Date of Patent: Feb. 13, 2001

(54) BENZYLMALTOSIDES AS INHIBITORS OF SMOOTH MUSCLE CELL PROLIFERATION

(75) Inventor: Paul J. Dollings, Newtown, PA (US)

(73) Assignee: American Home Products Corporation, Madison, NJ (US)

(*) Notice: Under 35 U.S.C. 154(b), the term of this patent shall be extended for 0 days.

(21) Appl. No.: 09/444,076

(22) Filed: Nov. 22, 1999

Related U.S. Application Data

(60) Provisional application No. 60/229,360, filed on Nov. 24, 1998.

(51) Int. Cl.$^7$ ............... A61K 31/7016; A61K 31/7028; A61K 31/7042; C07H 7/06; C07H 9/04
(52) U.S. Cl. ..................... 514/25; 536/4.1; 536/17.2
(58) Field of Search ................. 536/4.1, 17.2; 514/25

(56) References Cited

U.S. PATENT DOCUMENTS

| | | | |
|---|---|---|---|
| 2,752,334 | 6/1956 | Walton | 260/211 |
| 4,431,637 | 2/1984 | Upeslacis et al. | 424/180 |
| 5,019,562 | 5/1991 | Folkman et al. | 514/58 |
| 5,037,973 | 8/1991 | Meinetsberger | 536/53 |
| 5,296,588 | 3/1994 | Au et al. | 536/1.1 |
| 5,310,542 | 5/1994 | Au et al. | 424/52 |
| 5,336,765 | 8/1994 | Au et al. | 536/18.5 |
| 5,464,827 | 11/1995 | Soll | 514/58 |
| 5,498,775 | 3/1996 | Novak et al. | 514/25 |
| 5,773,420 | * 6/1998 | Nguyen et al. | 514/25 |

FOREIGN PATENT DOCUMENTS

| | | |
|---|---|---|
| 0312086 | 4/1989 | (EP). |
| 0312087 | 4/1989 | (EP). |
| 0454220 | 10/1991 | (EP). |
| 0551675 | 7/1993 | (EP). |
| 9006755 | 6/1990 | (WO). |
| 9309790 | 5/1993 | (WO). |
| 9614324 | 5/1996 | (WO). |
| 9614325 | 5/1996 | (WO). |

OTHER PUBLICATIONS

Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed., 1988, 37 (5), 654–657.
Zehavi, Carbohyd. Res., 1986, 151, 371.
Reilly et al., Drug Development Research, 1993, 29, 137.
Klein et al., Liebigs Ann. Chem., 1987, 485–489.
Durette et al., Carbohydrate Research, 1978, 67, 484–490.
Bertho, Liebigs Ann. Chem., 1949, 562, 229–239.
Kopper et al., Carbohydrate Research, 1989, 193, 296–302.

* cited by examiner

Primary Examiner—Kathleen K. Fonda
Assistant Examiner—Leigh C. Maier

(74) Attorney, Agent, or Firm—Arnold S. Milowsky

(57) ABSTRACT

This invention provides smooth muscle cell proliferation inhibitors of formula I having the structure

I wherein X is

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl;

$R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

$R^{11}$ is halogen, nitrile, nitro, or perfluoroalkyl of 1–6 carbon atoms; or a pharmaceutically acceptable salt thereof.

16 Claims, No Drawings

BENZYLMALTOSIDES AS INHIBITORS OF SMOOTH MUSCLE CELL PROLIFERATION

This application claims the benefit of U.S. Provisional Application No. 60/229,360, which was converted from U.S. Patent Application No. 09/198,434, filed Nov. 24, 1998, pursuant to a petition filed under 37 C. F. R. 1.53(c)(2)(i).

BACKGROUND OF THE INVENTION

This invention relates to the use of substituted benzylmaltosides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News,* 1993, June 28, 27).

WO 96/14325 discloses acylated benzylglycosides as smooth muscle cell proliferation inhibitors. The compounds of the present invention differ in that the substituents on the carbohydrate backbone are substantially different.

Zehavi, U., in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that (a) the substituents on the benzyl groups are different and (b) the use (smooth muscle antiproliferation) is different.

Patent numbers U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5019562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4431637 discloses polysulfated phenolic glycosides as modulators of the complement system. The compounds of the present invention differ from this prior art in that the compounds (a) are benzylmaltosides which bear no structural resemblance to heparin, sulfated cyclodextrins, or to sulfated lactobionic acid dimers, (b) contain no more than two contiguous sugar residues (disaccharide) and (c) are of a defined structure.

DESCRIPTION OF THE INVENTION

This invention provides benzylmaltosides of formula I

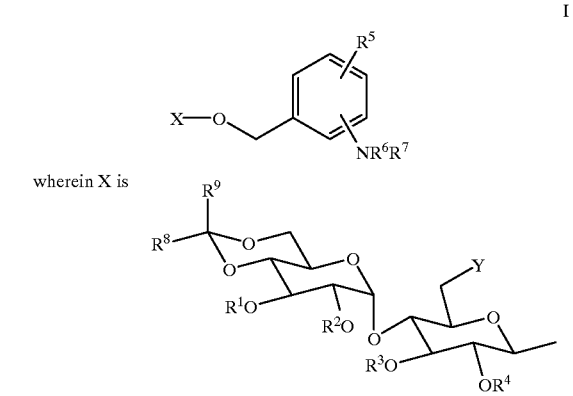

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl; $R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or-mercapto;

$R^{11}$ is halogen, nitrile, nitro, or perfluoroalkyl of 1–6 carbon atoms; or a pharmaceutically acceptable salt thereof.

Alkyl, alkoxy, alkylsulfonyl, acylamino, alkoxycarbonyl and acyl includes both straight chain as well as branched moieties optionally substituted with fluorine. Halogen means bromine, chlorine, fluorine, and iodine. Aryl is defined as a fully unsaturated carbocyclic radical containing one or more rings having 6–10 carbon atoms optionally substituted with fluorine; with phenyl and naphthyl radicals being preferred.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when the compound of formula I contains a basic nitrogen, and base addition salts can typically be prepared when the compound of formula I contains a hydroxyl group.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are benzylmaltosides of formula I

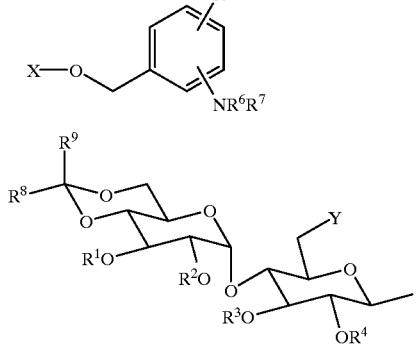

wherein X is

Y is hydrogen, halogen, azido, or Het optionally substituted with $R^{10}$;

Het is 1,3-dioxo-1,3-dihydro-isoindol-2-yl, or imidazol-1-yl;

$R^1$, $R^2$, $R^3$ and $R^4$, are each, independently, hydrogen, or acyl of 2–7 carbon atoms;

$R^5$ is hydrogen, alkyl of 1–6 carbon atoms, or halogen;

$R^6$ and $R^7$, are each, independently, hydrogen, or acyl of 2–7 carbon atoms;

$R^8$ and $R^9$, are each, independently, hydrogen, or aryl of 6–10 carbon atoms;

$R^{10}$ is halogen, nitrile, nitro, amino, acylamino of 2–7 carbon atoms, carboxyl, alkyl of 1–6 carbon atoms, alkoxy of 1–6 carbon atoms, or aryl of 6–10 carbon atoms;

or a pharmaceutically acceptable salt thereof.

More preferred compounds of this invention are benzylmaltosides of formula I

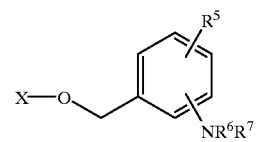

wherein X is

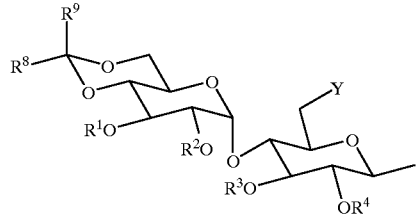

Y is hydrogen, iodo, azido, or Het optionally substituted with $R^{10}$;

Het is 1,3-dioxo-1,3-dihydro-isoindol-2-yl, or imidazol-1-yl;

$R^1$, $R^2$, $R^3$ and $R^4$, are each, independently, hydrogen, or acetyl;

$R^5$ is hydrogen, alkyl of 1–3 carbon atoms, or chloro;

$R^6$ is hydrogen;

$R^7$ is acetyl;

$R^8$ is phenyl;

$R^9$ is hydrogen;

$R^{10}$ is nitro;

or a pharmaceutically acceptable salt thereof.

Specifically preferred compounds of this invention are:

N-(5-{[4',6'-O-Benzylidene-6-deoxy-6-(4-nitro-1H-imidazol-1-yl)-β-D-maltosyl-oxy]-methyl}-2-methyl-phenyl)-acetamide or a pharmaceutically acceptable salt thereof;

N-(5-{[2,3,2',3'-Tetra-O-acetyl-4', 6'-O-benzylidene-6-deoxy-6-(4-nitro-1H -imidazol-1-yl)-β-D-maltosyl]-oxy-methyl}-2-chloro-phenyl)-acetamide or a pharmaceutically acceptable salt thereof;

N-(5-{[4',6'-O-Benzylidene-6-deoxy-6-(4-nitro-1H-imidazol-1-yl)-β-D -maltosyl]-oxy-methyl}-2-chloro-phenyl)-acetamide or a pharmaceutically acceptable salt thereof;

N-{5-[(2,2',3,3'-Tetra-O-acetyl-4',6',-O-benzylidene-6-deoxy-6-iodo-β-D -maltosyl)-oxy-methyl]-2-chloro-phenyl}-acetamide or a pharmaceutically acceptable salt thereof;

N-{5-[(4',6',-O-Benzylidene-6-deoxy-6-iodo-β-D-maltosyl)-oxy-methyl]-2-chloro-phenyl}-acetamide or a pharmaceutically acceptable salt thereof;

N-(5-{[2,2',3,3'-Tetra-O-acetyl-4',6'-O-benzylidene-6-deoxy-6-( 1,3-dioxo-1,3-dihydro-isoindol-2-yl)-β-D-maltosyl]-oxy-methyl}-2-chloro-phenyl)-acetamide or a pharmaceutically acceptable salt thereof;

N-(5-{[4',6'-O-Benzylidene-6-deoxy-6-( 1,3-dioxo-1,3-dihydro-isoindol-2-yl)-β-D-maltosyl]-oxy-methyl}-2-chloro-phenyl)-acetamide or a pharmaceutically acceptable salt thereof; and N-{5-[(6-Deoxy-6-O-azido-4',6'-O-benzylidene-β-D-maltosyl)-oxy-methyl]-2-chloro-phenyl}-acetamide or a pharmaceutically acceptable salt thereof.

The compounds of this invention were be prepared according to the following schemes from commercially available starting materials or starting materials which can be prepared using literature procedures. This scheme shows the preparation of representative compounds of this invention.

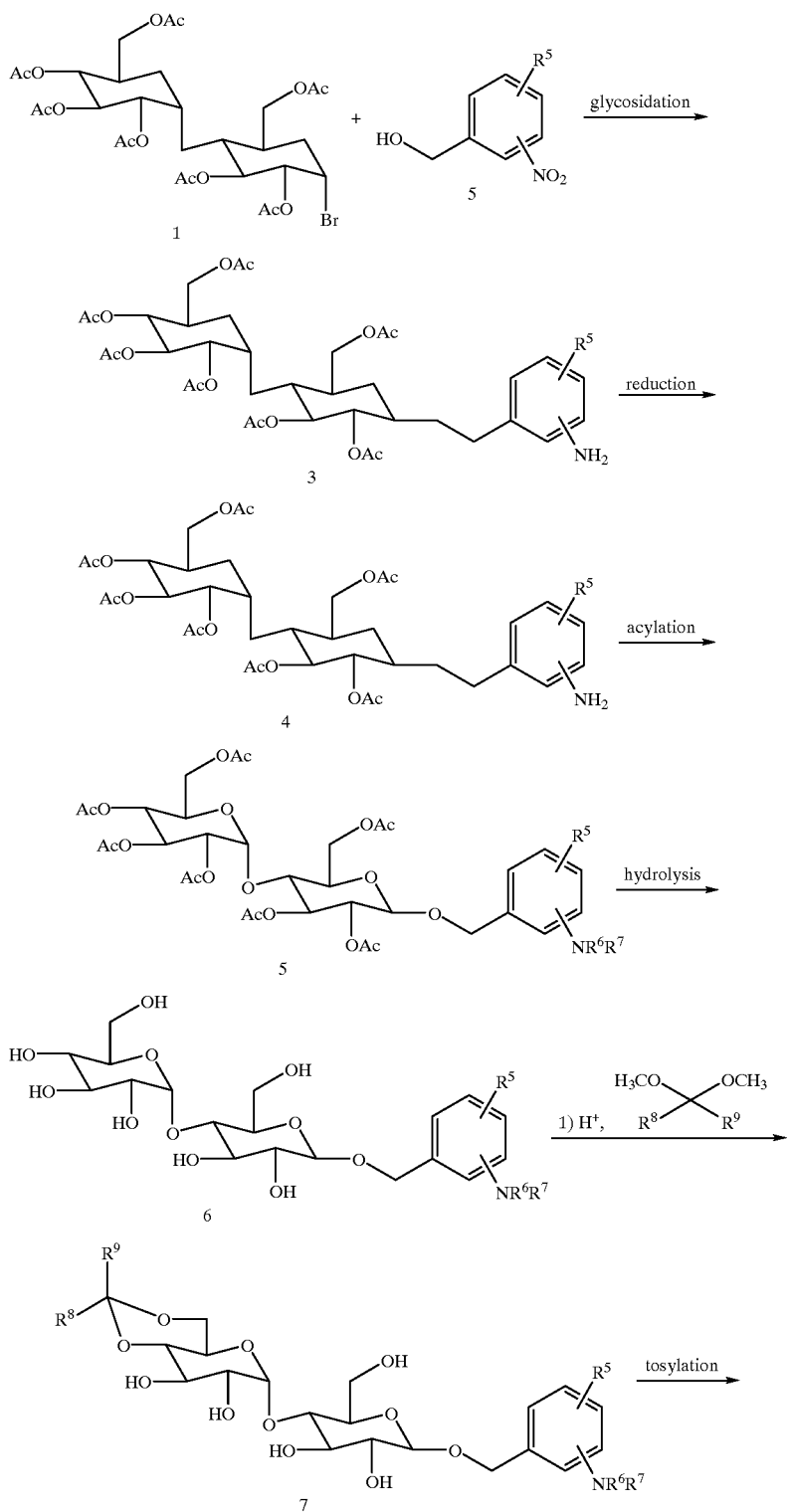

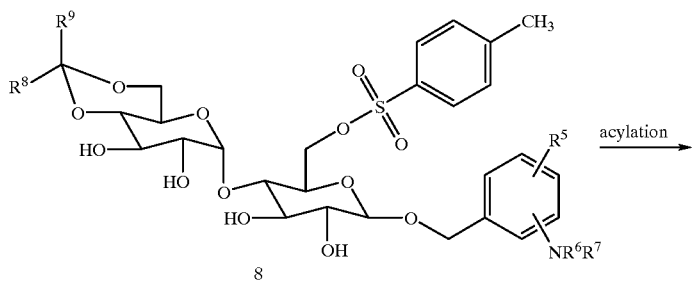

8

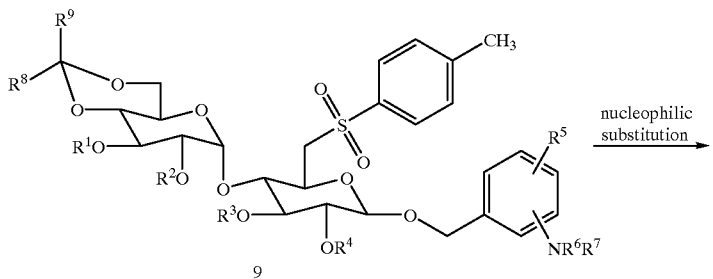

9

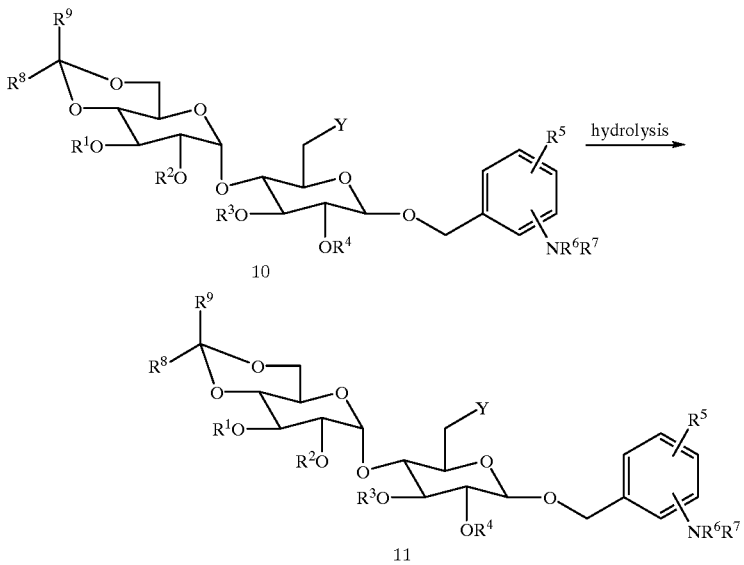

10

11 where Y and $R^1$, $R^2$, $R^3$, $R^4$, $R^5$, $R^6$, $R^7$, $R^8$ and $R^9$ are as defined above.

Thus, maltosyl bromide 1 is coupled with a benzyl alcohol 2 in the presence of a catalyst such as a mercuric bromide, mercuric cyanide, silver triflate or silver perchlorate in an aprotic solvent such as acetonitrile, dichloromethane, ether, toluene or nitromethane at temperatures ranging from −40° C. to reflux to yield glycoside 3. Reduction of the nitro group of 3 can be accomplished with a reducing agent such as stannous chloride in a polar aprotic solvent such as such as ethyl acetate at ambient temperature to reflux or by catalytic hydrogenation in the presence of a catalyst such as palladium on carbon to give the anilino compound 4. Coupling of 4 with an acid chloride can be completed in the presence of an amine base such as triethylamine, diisopropylethylamine or pyridine in an aprotic solvent such as dichloromethane or tetrahydrofuran at temperatures ranging from −20° C. to ambient temperature to give the amide 5. The acetate groups of 5 can be replaced by hydrolysis with a base such as sodium methoxide in methanol or aqueous sodium hydroxide in methanol at ambient temperature to reflux to yield 6. The 4'and 6'groups can be reacted with an acetal in the presence of an acid catalyst such as camphorsulfonic acid or p-toluene sulfonic acid in a polar aprotic solvent such as N,N-dimethylformamide at temperatures ranging from 25° C. to reflux to give the acetal/ketal derivative 7. Selective tosylation at position 6 can be accomplished in the presence of a p-toluenesulfonyl chloride and an amine base such as triethylamine, diisopropylethylamine or pyridine in an aprotic solvent such as dichloromethane or tetrahydrofuran at temperatures ranging from −20° C. to 5° C. to give the tosylate 8 and reacylation with an acyl anhydride in the presence of an amine base such as pyridine at temperatures ranging from 0° C. to ambient temperature to yield 9. The tosylate 9 can be substituted with an appropriate nucleophile, which can be generated with a base such as sodium hydride or potassium carbonate in a polar aprotic solvent such as N,N-dimethylformamide at ambient temperature to give 10. The acetate groups of 10 can be replaced by hydrolysis with a base such as sodium methoxide in methanol or aqueous sodium hydroxide in methanol at ambient temperature to reflux to yield 11. Alternatively, the tosylate 8 can be substituted directly, without protection of hydroxyl groups, to yield 11.

The compounds of this invention are useful as antiproliferative agents. The following procedures show the evaluation of representative compounds of this invention in standard pharmacological test procedure which measured ability of the evaluated compound to inhibit smooth muscle cell proliferation Effects of Compounds on Cell Proliferation Using $^3$H Thymidine Incorporation Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic / antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum / growth factor to serum deprived synchronized cells and results are reported accordingly.

Compounds were added to each well at 50 fold dilution (20 AL / well) and the plates were incubated for 24–36 h at 37° C. in 5% $CO_2$. Compounds were initially dissolved in 50% ethanol and serially diluted into media. Compounds were routinely evaluated at concentrations from 1 to 100 $\mu$M. As a control, grade II porcine intestinal mucosal heparin (sodium salt) was routinely evaluated in all cell preparations at concentrations from 0.1 to 100 $\mu$g/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 $\mu$L/ vial to neutralize NaOH) and each well was rinsed two times with water (500 $\mu$L) for a total volume of 2 mL / vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ in Table I below.

TABLE 1

| Compound of Example | Porcine Smooth Muscle Cell Antiproliferation IC50 |
| --- | --- |
| 1 | 11.0 $\mu$M |
| 2 | 0.807 $\mu$M |
| 3 | 1.85 $\mu$M |
| 4 | 0.20 $\mu$M |
| 5 | 1.16 $\mu$M |
| 6 | 0.84 $\mu$M |
| 7 | 1.59 $\mu$M |
| 8 | 0.614 $\mu$M |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation include hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

N-(5-{[4',6'-O-Benzylidene-6-deoxy-6-(4-nitro-1H-imidazol-1-yl)-β-D-maltosyl-oxy]-methyl}-2-methyl-phenyl)-acetamide

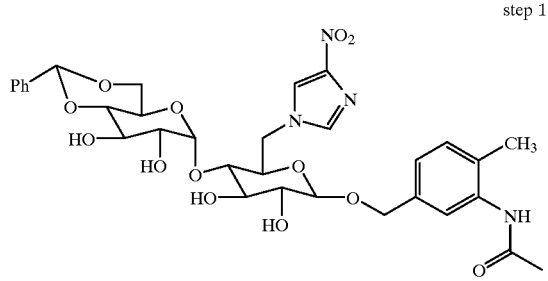

5-(Hepta-O-acetyl-β-D-maltosyloxymethyl)-2-methyl-1-nitrobenzene

At ambient temperature, to a stirred solution of acetobromomaltose (15.0 g, 0.0193 mol), 4-methyl-3-nitrobenzyl alcohol (4.18 g, 0.0251 mol) and HgBr$_2$ (9.02 g, 0.0251 mol) in freshly distilled CH$_3$CN (129 mL) was added in one portion Hg(CN)$_2$ (6.34 g, 0.0251 mol). After 2.5 h, brine (250 mL) was added and the mixture was extracted with EtOAc. The combined organic extracts were washed with brine, dried (MgSO$_4$) and concentrated. Purification by flash chromatography ( 30% acetone/hexane) gave 8.02 g (53%) of title compound as a white solid, mp 68–74 ° C.; $^1$H NMR (DMSO-d$_6$) δ1.931 (s, 3 H), 1.939 (s, 3 H), 1.947 (s, 3 H), 1.967 (s, 3 H), 1.972 (s, 3 H), 2.012 (s, 3 H), 2.073 (s, 3 H), 3.93–4.01 (m, 4 H), 4.13–4.21 (m, 2 H), 4.37 (d, 2 H), 4.64–4.90 (m, 5 H), 4.97 (t, 1 H), 5.20 (dd, 1 H), 5.27–5.33 (m, 2 H), 7.48 (d, 1 H), 7.52 (d, 1 H), 7.88 (s, 1 H). IR (KBr) 2950, 1750, 1230 and 1050 cm$^{-1}$, mass spectrum (FAB), m/z 808 (M+H). Anal. Calcd. for C$_{34}$H$_{43}$NO$_{20}$: C, 51.98; H,5.52; N, 1.78. Found: C, 51.59; H, 5.45; N, 1.86.

Step 1

5-(Hepta-O-acetyl-,β-D-maltosyloxymethyl)-2-methylphenylamine

A solution containing 5 -(hepta-O-acetyl-β-D-maltosyloxymethyl)-2-methyl-1-nitrobenzene (7.11 g, 9.05 mmol) and tin (II) chloride dihydrate ( 14.3 G, 63.3 mmol) in EtOAc (181 mL) was refluxed for 2 h. The reaction was cooled to room temperature, carefully quenched with sat. aq. NaHCO$_3$ (until basic), diluted with EtOAc (250 mL), stirred for 0.5 h and filtered. The biphasic filtrate was separated and the aqueous phase extracted with EtOAc. The combined organic extracts were dried (K$_2$CO$_3$) and concentrated. Purification by flash chromatography (0,1,2 and 3% MeOH/CHCl3 gradient) gave 5.39 g ( 79%) of 5-(Hepta-O-acetyl-β-maltosyloxymethyl)-2-methylphenylamine as a white foam; $^1$H NMR (DMSO-d$_6$) δ1.93 (s, 3 H), 1.94 (s, 3 H), 1.95 (s, 3 H), 1.97 (s, 3 H), 1.98 (s, 3 H), 2.03 (s. 6 H), 2.10 (s, 3 H), 3.93–4.03 (m, 4 H), 4.14–4.23 (m, 2 H), 4.32–4.41 (m, 2 H), 4.58 (d, 1 H), 4.68 (t, 1 H), 4.76–4.88 (m, 4 H), 4.98 (t, 1 H), 5.22 (t, 1 H), 5.28–5.31 (m, 2 H), 6.37 (d, 2 H), 6.49 (s, I H), 6.87 (d, 1 H)

Step 2

N-[5-(Hepta-O-acetyl-β-D-maltosyloxymethyl)-2-methylphenyl]acetamide

At ambient temperature, to a stirred solution of 5-(hepta-O-acetyl-β-D-maltosyloxymethyl)-2-methylphenylamine (6.88 g, 9.10 mmol) and triethylamine (4.18 mL, 30.0 mmol) in THF (91 mnL) was added dropwise acetyl chloride (0.714 mL, 10.0 mmol). After 4 h, the reaction was quenched with sat. aq. NaHCO$_3$ (100 mL), diluted with brine (100 mL) and extracted with EtOAc. The combined organic extracts were dried (K$_2$CO$_3$) and concentrated. Purification by flash chromatography (1,2 and 3% MeOH/CHCl3 gradient) gave 6.60 g (91%) of N-[5-(Hepta-O-acetyl-β-maltosyloxymethyl)-2-methylphenyl]acetamide as a white foam; $^1$H NMR (DMSO-d$_6$) δ1.93 (s, 3 H), 1.94 (s, 3 H), 1.95 (s, 3 H), 1.979 (s, 3 H), 1.984 (s, 3 H), 2.03 (s, 3 H), 2.10 (s, 3 H), 2.18 (s, 3 H), 3.9–4.02 (m, 4 H), 4.14 4.24 (m, 2 H), 4.40 (d, 1 H), 4.48 (d, 1 H), 4.67–4.74 (m 2 H), 4.81–4.89 (m 2 H), 4.98 (t, 1 H), 5.19–5.32 (m, 3 H), 6.98 (d, 1 H), 7.17 (d, I H), 7.33 (s, 1 H), 9.27 (s, 1 H)

Step 3

N-[5-(β-D-Maltosyloxy-methyl)-2-methyl-phenyl]-acetamide

A solution containing N-[5-(hepta-O-acetyl-β-D-maltosyloxymethyl)-2-methylphenyl]acetamide (6.60 g, 8.27 mmol) and 25 weight % NaOMe in MeOH (0.893 g, 4.14 mmol) in MeOH (198 mL) was refluxed for 2.5 h. The reaction was cooled to room temperature and concentrated to give 4.09 g (98%) of N-[5-β-Maltosyloxy-methyl)-2-methyl-phenyl]-acetamide as a white foam. This material was used without any additional purification.

An analytical sample was obtained by reverse phase HPLC (C 18, 15% CH$_3$CN/H$_2$O) to give a white solid, mp 115° C.; $^1$H NMR (DMSO-d$_6$)β2.03 (s, 3 H), 2.16 (s, 3 H), 3.04–3.09 (m, 2 H), 3.21–3.56 (m, 7 H), 3.57–3.62 (m, 2H), 3.70–3.73 (m, 1 H), 4.26 (d, 1 H), 4.48–4.54 (m, 3 H), 4.76 (d, 1 H), 4.86–4.89 (m, 2 H), 5.01 (d, 1 H), 5.17 (d, 1 H), 5.42 (d, 1 H), 5.49 (d, 1 H), 7.10 (d, 1 H), 7.15 (d, 1 H), 7.35 (s, 1 H), 9.28 (s, 1 H). IR (KBr) 3375, 2900, 1670 and 1025 cm$^{-1}$, mass spectrum (FAB), m/z 504 (M+H), 526 (M+Na). Anal. Calcd. for C$_{22}$H$_{33}$NO$_{12}$ 0.5 H$_2$O: C, 51.56; H, 6.67; N, 2.73. Found: C, 51.78; H, 6.81; N, 2.75.

Step 4

N-{5-[(4',6'-O-Benzylidene-β-D-maltosyl-oxy)-methyl]-2-methyl-phenyl}-acetamide

A solution containing N-[5-(β-D-maltosyloxy-methyl)-2-methyl-phenyl]-acetamide (1.88 g, 3.83 mmol), benzaldehyde dimethyl acetal (0.807 mL, 5.36 mmol) and p-toluenesulfonic acid monohydrate (72.7 mg, 0.383 mmol) was heated at 60° C. After 4 h, additional benzaldehyde dimethyl acetal (0.403 muL, 2.68 mmol) and toluenesulfonic acid monohydrate (36.4 mg, 0.192 mmol) was added and the reaction was heated at 60° C. for 16 h. To the reaction was added K$_2$CO$_3$ and heating was continued for 0.5 h. The hot solution was filtered and the filtrate concentrated. Purification by reverse phase HPLC (C18, 15% CH$_3$CN/H$_2$O) gave 1.26 g (56%) of the title compound as a white solid, mp 190–197° C.; $^1$H NMR (DMSO-d$_6$)β2.04 (s, 3 H), 2.16 (s, 3 H), 3.08 (t, 1 H), 3.35–3.40 (m, 3 H), 3.45 (t, 1 H), 3.53–3.59 (m, 2 H), 3.6–3.75 (m, 3 H), 4.11 (dd, J=5.1, 2.4 Hz, 1 H), 4.28 (d, 1 H), 4.50 (d, 1 H), 4.67 (t, 1 H), 4.77 (d, 1 H), 5.13 (d, 1 H), 5.21 (br. s, 1 H), 5.29 (br. s, 1 H), 5.49 (br. s, 1 H), 5.57 (s, 1 H), 5.61 (br. s, 1 H), 7.10 (d, 1 H), 7.16 (d, 1 H), 7.3–7.38 (m, 4 H), 7.42–7.45 (s, 2 H), 9.28 (s, 1 H). IR (KBr) 3400, 2900, 1650 and 1075 cm$^{-1}$, mass spectrum (+ESI), m/z 609 (M+NH 4), 614 (M+Na). Anal. Calcd. for C$_{29}$H$_{37}$NO$_{12}$ 0.5 H$_2$O: C, 57.99; H, 6.30; N, 2.37. Found: C, 57.80; H, 6.39; N, 2.50. Found: C, 57.85; H, 6.33; N, 2.27.

Step 5

N-(5-[4',6'-O-Benzylidene-6-O-(4-toluenesulfonyl)-β-D-maltosyl-oxy]-methyl-2-methyl-phenyl)-acetamide At 0° C., to a stirred solution of N-{5-[(4',6'-O-benzylidene-β-D-maltosyl-oxy)-methyl]-2-methyl-phenyl}-acetamide (0.711 g, 1.20 mmol) in pyridine (2.4 mL) was added a solution of p-toluenesulfonyl chloride (0.275 g, 1.44 mmol) in CH$_2$Cl$_2$ (1.5 mL). After 2 h, additional p-toluenesulfonyl chloride (0.275 g, 1.44 mmol) in CH$_2$Cl$_2$ (1.5 mL) was added and the solution was stirred at 0° C. for 2 h. The reaction was quenched with ice cold H$_2$O (50 mL) and extracted with EtOAc. The combined organic extracts were washed successively with sat. aq. NaHCO$_3$ (2×), sat. aq. CuSO$_4$ (2×), brine (2×), dried (Na$_2$SO$_4$) and concentrated. Purification by reverse phase HPLC (C18, 50% CH$_3$CN/H$_2$O) gave 4.21 g, (47%) of a white solid. mp 115–121° C.; $^1$H NMR (DMSO-d$_6$) δ2.05 (s, 3 H), 2.17 (s, 3 H), 2.33 (s, 3 H), 3.05 (t, 1 H0, 3.24–3.44 (m, 4 H), 3.52 (t, 1 H), 3.58–3.62 (m, 3 H), 3.95 (d, 1 H), 4.13 (dd, 1 H), 4.28 (d, 1), 4.33 (d, 1 H), 4.41 (d, 1 H), 4.59 (d, 1 H), 5.05 (d, 1 H), 5.57 (s, 1 H), 7.06 (d, 1 H), 7.16 (d, 1 H), 7.33–7.47 (m 8 H), 7.78 (d, 2 H), 9.29 (s, 1 H). IR (KBr) 3375, 2900, 1650, 1350, 1175 and 1075 cm$^{-1}$, mass spectrum (FAB), m/z 746 (M+H), 768 (M+Na). Anal. Calcd. for C$_{36}$H$_{43}$NO$_{14}$S H$_2$O: C, 56.61; H, 5.94; N, 1.83. Found: C, 56.61; H, 5.77; N, 1.80.

Step 6

N-(5-{[4',6'-O-Benzylidene-6-deoxy-6-(4-nitro-1H-imidazol-1-yl)-δ-D-maltosyl-oxy]-methyl}-2-methyl-phenyl)-acetamide To a stirred solution of 4-nitroimidazole (51.5 mg, 0.456 mmol) in DMF (1.5 mL) at ambient temperature was added K$_2$CO$_3$ (28.6 mg, 0.207 mmol). After 0.5 h, to the reaction was added a solution of N-(5-[4',6'-O-benzylidene-6-O-(4-toluenesulfonyl)-δ-D-maltosyl-oxy]-methyl-2-methyl-phenyl)-acetamide (0.309 g, 0.414 mmol) in DMF (4.5 mL) and the reaction was heated at 100° C. for 4 h. The reaction was cooled to room temperature, quenched with ice cold H$_2$O (40 mL) and extracted with EtOAc. The organic extracts were dried (Na$_2$SO$_4$) and concentrated. Purification by reverse phase HPLC (C18, 35% CH$_3$CN/H$_2$O) followed by crystallization from EtOAc/hexane gave 73 mg, (26%) of a white solid. mp 158° C.; $^1$H NMR (DMSO-d$_6$) δ2.04 (s, 1 H), 2.15 (s, 1 H), 3.08 (t, 1 H), 3.24–3.49 (m, 4 H), 3.62 (d, 1 H), 3.65 (d, 1 H), 3.76 (t, 1 H), 3.87–3.93 (m, 1 H), 4.23–4.34 (m, 4 H), 4.47–4.51 (m, 2 H), 5.20 (d, 1 H), 5.37 (br.s, 2 H), 5.58 (br. s, 1 H), 5.59 (s, 1 H), 5.88 (br. s, 1 H), 6.91 (d, 1 H), 7.12 (d, 1 H), 7.21 (s, 1 H), 7.36–7.40 (m, 3 H), 7.44–7.47 (m, 2 H), 7.81 (s, 1 H), 8.39 (s, 1 H), 9.27 (s, 1 H). IR (KBr) 3375, 2925, 1660, 1550, 1500, 1375, 1350, 1300 and 1075 cm$^{-1}$, mass spectrum (FAB), m/z 687 (m+H). Anal. Calcd. for C$_{32}$H$_{38}$N$_4$O$_{13}$ 0.9 H$_2$O: C, 54.68; H, 5.71; N, 7.97. Found: C, 54.97; H, 5.47; N, 7.58.

EXAMPLE 2

N-(5-{[2,3,2',3'-Tetra-O-acetyl-4',6'-O-benzylidene-6-deoxy-6-(4-nitro-1H-imidazol-1-yl)-δ-D-maltosyl]-oxy-methyl}-2-chloro-phenyl)-acetamide

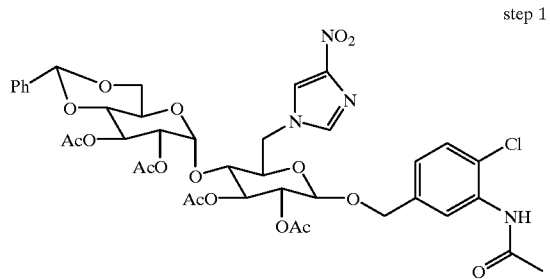

step 1

Step 1

N-(5-{[4',6'-O-Benzylidene-6-O-(4-toluenesulfonyl)-β-D-maltosyl]-oxy-methyl}-2-chloro-phenyl)-acetamide At 0° C., to a stirred solution of N-{5-[(4',6'-O-benzylidene-β-D-maltosyl)-oxy-methyl]-2-chloro-phenyl}-acetamide, prepared according to the procedures in Example 1 and using 4-chloro-3-nitrobenzyl alcohol in step 1 (1.50 g, 2.86 mmol) in pyridine (5.7 mL) was added a solution of p-toluenesulfonyl chloride (0.657 g, 3.44 mmol) in CH$_2$Cl$_2$ (3 niL). After 2 h, the reaction was quenched with ice cold H$_2$O (50 mL), diluted with brine (10 mL) and extracted with EtOAc. The combined organic extracts were washed successively with sat. aq. NaHCO$_3$ (3×), sat. aq. CuSO$_4$ (3×), brine (3×), dried (Na$_2$SO$_4$) and concentrated. Purification by flash chromatography (5 and 10% MeOH/CH$_2$Cl$_2$ gradient) gave 0.903 g (41%) of title compound as a white solid, mp 105–120° C.; $^1$H NMR (DMSO-d$_6$) δ2.08 (s, 3 H), 2.33 (s, 3 H), 3.04–3.09 (m, 1 H), 3.27–3.45 (m, 4 H), 3.49–3.53 (m, 1 H), 3.60–3.65 (m, 3 H), 3.95 (d, 1 H), 4.13 (dd, 1 H), 4.29–4.33 (m, 2 H), 4.46 (d, 1 H), 4.62 (d, 1 H), 5.05 (d, 1 H), 5.333–5.35 (m, 2 H), 5.55 (d, 1 H), 5.57 (s, 1 H), 5.75 (d, 1 H), 7.18 (d, 1 H), 7.35–7.47 (m, 8 H), 7.78 (d, 2 H), 9.53 (s, 1 H). mass spectrum (+ESI), m/z 766/768 (M+H), 783/785 (M+NH 4). Anal. Calcd. for $C_{35}H_{40}NClO_{14}S \cdot H_2O$: C, 53.60; H, 5.40; N, 1.79. Found: C, 53.46; H, 5.18; N, 1.80.

Step 2

N-(5-{[2,3,2',3'-Tetra-O-acetyl-4',6'-O-benzylidene-6-O-(4-toluenesulfonyl)-β-D-maltosyl]-oxy-methyl}-2-chloro-phenyl)-acetamide At 0° C., to a stirred solution containing N-(5-{[4',6'-O-benzylidene-6-O-(4-toluenesulfonyl)-β-D-maltosyl]-oxy-methyl}-2-chloro-phenyl)-acetamide (0.782 g, 1.02 mmol), pyridine (0.991 mL, 12.3 mmol) and 4-dimethylaminopyridine (0.457 g, 4.08 mmol) in $CH_2Cl_2$ (20 mL) was added acetic anhydride (0.764 mL, 8.17 mmol). After 2 h, the reaction was diluted with diethyl ether (100 mL), washed successively with $H_2O$ (2×), with sat. aq. $NaHCO_3$ (2×), with sat. aq. $CuSO_4$ (2×), with brine (2×), dried ($Na_2SO_4$) and concentrated. Purification by flash chromatography (1,2 and 3% $MeOH/CHCl_3$ gradient) gave 0.942 g (99%) of title compound as a white solid, mp 116–122° C.; $^1H$ NMR (DMSO-$d_6$) δ1.91 (s, 3 H), 1.92 (s, 3 H), 1.96 (s, 3 H), 2.00 (s, 3 H), 2.08 (s, 3 H), 2.29 (s, 3 H), 3.68 (dd, 1 H), 3.77 (t, 1 H), 3.85 (t, 1 H), 3.90 (t, 1 H), 3.97–4.00 (m, 1 H), 4.21 (dd, 1 H), 4.32 (s, 2 H), 4.39 (d, 1 H), 4.56 (d, 1 H), 4.60 (d, 1 H), 4.78 (d, 1 H), 4.86 (dd, 1 H), 5.17–5.30 (m, 3 H), 5.65 (s, 1 H), 7.03 (d, 1 H), 7.3–7.41 (m, 7 H), 7.46 (d, 1 H), 7.59 (s, 1 H), 7.80 (d, 2 H), 9.52 (s, 1 H). mass spectrum (+ESI), m/z 934/936 (M+H). Anal. Calcd. for $C_{43}H_{48}NClO_{18}S$: C, 55.27; H, 5.17; N, 1.50. Found: C, 55.07; H, 5.05; N, 1.47.

Step 3

N-(5-{[2,3,2',3'-Tetra-O-acetyl-4',6'-O-benzylidene-6-deoxy-6-(4-nitro-1 H-imidazol-1-yl)-β-D-maltosyl]-oxy-methyl}-2-chloro-phenyl)-acetamide At ambient temperature, to a solution of 4-nitroimidazole (41.0 mg, 0.363 mmol) in DMF (1 mL) was added 60% sodium hydride/mineral oil (13.2 mg, 0.330 mmol) and the mixture was stirred for 0.5 h. To the reaction was added a solution of N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.308 g, 0.330 mmol) in DMF (1.5 mL) and the reaction was heated at 100° C. for 16 h. The reaction was cooled to room temperature, quenched with ice cold $H_2O$ (50 mL) and extracted with EtOAc. The organic extracts were dried ($Na_2SO_4$) and concentrated. Purification by flash chromatography (1,2 and 3% $MeOH/CHCl_3$ gradient) followed by crystallization from $CH_2CL_2$/pet. ether gave 0.110 g (38%) of title compound as a white solid, mp 132–142° C.; $^1H$ NMR (DMSO-$d_6$) δ1.93 (s, 3 H), 1.93 (s, 3 H), 1.97 (s, 3 H), 2.01 (s, 3 H), 2.07 (s, 3 H), 3.78 (t, 1 H), 3.87–3.95 (m, 3 H), 4.11 (t, 1 H), 4.27 (d, 1 H), 4.31–4.37 (m, 2 H), 4.46 (d, 1 H), 4.65–4.76 (m, 3 H), 4.96 (dd, J=5.9, 4.4 Hz, 1 H), 5.24 (t, 1 H), 5.30 (d, 1 H), 5.38 (t, 1 H), 5.65 (s, 1 H), 6.86 (dd, 1 H), 7.34–7.41 (m, 6 H), 7.49 (s, 1 H), 7.87 (s, 1 H), 8.48 (s, 1 H), 9.50 (s, 1 H). IR (KBr) 3400, 2925, 1760, 1375, 1230 and 1050 cm$^{-1}$. mass spectrum (+FAB), m/z 875/877 (M+H). Anal. Calcd. for $C_{39}H_{43}N_4ClO_{17}$: C, 53.52; H, 4.95; N, 6.40. Found: C, 53.25; H, 4.85; N, 6.03.

EXAMPLE 3

N-(5-{[4',6'-O-Benzylidene-6-deoxy-6-(4-nitro-1H-imidazol-1-yl)-β-D-maltosyl]-oxy-methyl}-2-chloro-phenyl)-acetamide

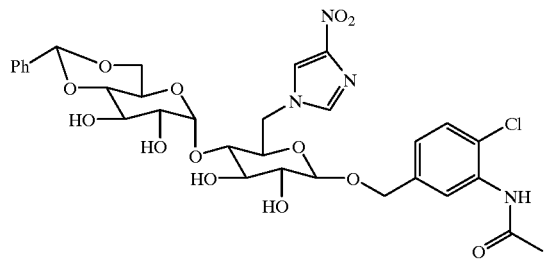

A stirred solution containing N-(5-{[2,3,2',3'-tetra-O-acetyl-4',6'-O-benzylidene-6-deoxy-6-(4-nitro-1H-imidazol-1-yl)-β-D-maltosyl]-oxy-methyl}-2-chloro-phenyl)-acetamide (0.208 g, 0.238 mmol) and 25 wt.% sodium methoxide in methanol (25.7 mg, 0.119 mmol) in MeOH (6.24 mL) was heated at 65° C.. After 3 h, the reaction was cooled to ambient temperature and concentrated in vacuo. Purification by flash chromatography (10% $MeOH/CHCl_3$) followed by crystallization from $CH_2Cl_2$/pet. ether gave 0.133 g (79%) as a white solid, mp 144–151° C.; $^1H$ NMR (DMSO-$d_6$) δ2.08 (s, 3 H), 3.06–3.12 (1 H), 3.28 (m, 1 H), 3.99–3.51 (m, 3 H), 3.61–3.69 (m, 2 H), 3.77–3.82 (m, 1 H), 3.87–3.93 (m, 1 H), 4.23–4.31 (m, 3 H), 4.39 (d, 1 H), 4.47 (dd, 1 H), 4.54 (d, 1 H), 5.20 (d, 1 H), 5.35 (d, 1 H), 5.36 (d, 1 H), 5.56–5.59 (m, 2 H), 7.05 (dd, 1 H), 7.35–7.48 (m, 6 H), 7.54 (s, 1 H), 7.80 (s, 1 H), 8.37 (s, 1 H), 9.50 (s, 1 H). IR (KBr) 3400, 2900, 1690, 1540, 1300 and 1065 cm$^{-1}$. mass spectrum (+FAB), m/z 707/709 (M+H). Anal. Calcd. for $C_{31}H_{35}N_4ClO_{13} \cdot H_2O$: C, 51.35; H, 5.14; N, 7.73. Found: C, 51.16; H, 5.07; N, 7.36.

EXAMPLE 4

N-{5-[(2,2',3,3'-Tetra-O-acetyl-4',6',-O-benzylidene-6-deoxy-6-iodo-β-D-maltosyl)-oxy-methyl]-2-chloro-phenyl}-acetamide

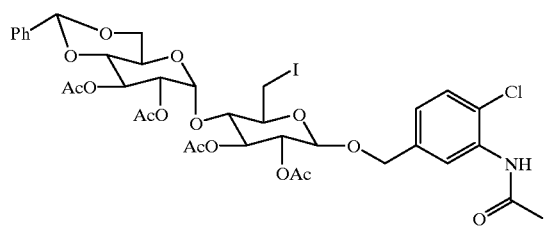

A solution containing N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (1.026 g, 1.098 mmol) and sodium iodide (1.646 g, 10.98 mmol) in DMSO (11 niL) was heated at 85° C. for 1 h. The reaction was cooled to room temperature and poured into $H_2O$ (110 nL). The resulting precipitate was collected, dissolved in $CH_2Cl_2$, dried ($Na_2SO_4$) and concentrated. Purification by flash chromatography (40% acetone/hexane) and crystallization from EtOAc/hexane gave 0.723 g (74%) of title compound as a white solid, mp 133–138° C.; $^1H$ NMR (DMSO-$d_6$) δ1.92 (s, 3 H), 1.94 (s, 3 H), 1.98 (s, 3 H), 2.00 (s, 3 H), 2.07 (s, 3 H), 3.48 (dd, J=10.5, 5.7 Hz, 1 H), 3.62–3.70 (m, 2 H), 3.74–3.82 (m 3 HO, 3.92 (t, J=9.0 Hz, 1 H), 4.33 (d,J=5.3 Hz, 1 H), 4.58 (d, J=12.7 Hz, 1 H), 4.65–4.70 (m, 1 H), 4.76 (d, J=12.7 Hz, 1 H), 4.87–4.93 (m, 2 H), 5.27 (t, J=9.9 Hz, 1 H), 5.31 (d, J=4.2 Hz, 1 H), 5.35 (t, J=9.0 Hz, 1 H), 5.64 (s, 1 H), 7.09 (dd, J=8.3, 1.8 Hz, 1 H), 7.35–7.39 (m, 5 H), 7.46 (d, J=8.1 Hz, 1 H), 7.65 (s, 1 H), 9.52 (s, 1 H). IR (KBr) 3400, 2950, 1750, 1375, 1240 and 1050 cm$^{-1}$. mass spectrum (+FAB), m/z 890/892 (M+H). Anal. Calcd. for $C_{36}H_{41}NClO_{15}$: C, 48.58; H, 4.64; N, 1.57. Found: C, 48.82; H, 4.61; N, 1.50.

EXAMPLE 5

N-{5-[(4',6',-O-Benzylidene-6-deoxy-6-iodo-β-D-maltosyl)-oxy-methyl]-2-chloro-phenyl}-acetamide

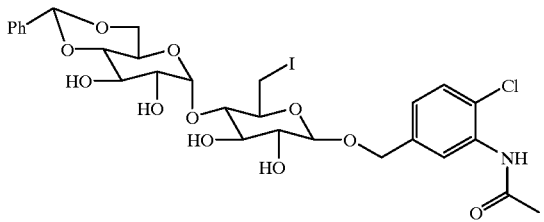

Using N-(5-{[4',6'-O-benzylidene-6-O-(4-toluenesulfonyl)-β-D-maltosyl]-oxy-methyl}-2-chloro-phenyl)-acetamide (0.201 g, 0.262 mmol) the title compound was prepared according to the procedure of Example 4. Purification was achieved by flash chromatography (10% MeOH/CH$_2$Cl$_2$) followed by crystallization from EtOAc/hexane gave 0.090 g (70%) of title compound as a white solid, mp 115–130° C.; $^1$H NMR (DMSO-d$_6$) δ2.07 (s, 3 H), 3.08–3.13 (m, 1 H), 3.28–3.29 (m, 2 H), 3.37–3.40 (m, 3 H), 3.50–3.61 (m, 3 H), 3.67–3,74 (m, 2 H), 4.10–4.14 (m, 1 H), 4.39 (d, 1 H), 4.69 (ABq, J=12.4 Hz, Δδ=0.08, 2 H), 5.19 (d, 1 H), 5.32–5.36 (m, 2 H), 5.51 (d, 1 H), 5.58 (s, 1 H), 5.60 (d, 1 H), 7.23 (dd, 1 H), 7.35–7.40 (m, 3 H), 7.42–7.46 (m, 3 H), 7.67 (s, 1 H), 9.52 (s, 1 H). IR (KBr) 3400, 2900, 1675, 1540, 1420 and 1070 cm$^{-1}$. mass spectrum (+FAB), m/z 722/724 (M+H). Anal. Calcd. for $C_{28}H_{33}NClO_{11}$: C, 46.59; H, 4.61; N, 1.94. Found: C, 46.21; H, 4.66; N, 2.04.

EXAMPLE 6

N-(5-{[2,2',3,3'-Tetra-O-acetyl-4',6'-O-benzylidene-6-deoxy-6-(1,3-dioxo-1,3-dihydro-isoindol-2-yl)-β-D-maltosyl]-oxy-methyl}2-chloro-phenyl)-acetamide

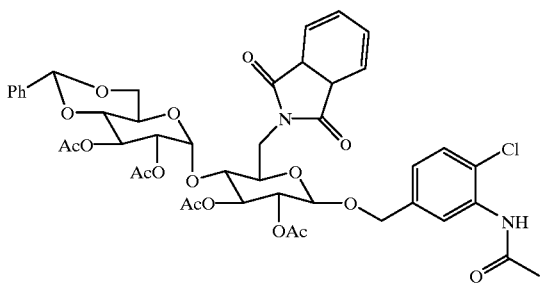

A solution containing N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.654 g, 0.700 mmol) and phthalimide potassium salt (0.142 g, 0.770 mmol) in DMF (7.0 niL) was heated at 100° C. for 1 h. The reaction was cooled to room temperature and poured into H$_2$O (70 mL). The resulting precipitate was collected, dissolved in CH$_2$Cl$_2$, washed with H$_2$O (1x), dried (Na$_2$SO$_4$) and concentrated. Purification by flash chromatography (40% acetone/hexane) gave 0.246 g (39%) of title compound as a white solid, mp 210–215° C.; $^1$H NMR (DMSO-d$_6$) δ1.93 (s, 3 H), 1.94 (s, 3 H), 2.00 (s, 3 H), 2.10 (s, 3 H), 2.05 (s, 3 H), 3.78 (t, J=9.6 Hz, 1 H), 3.91–4.03 (m, 6 H), 4.25 (d, J=12.5 Hz, 1 H), 4.31 (dd, J=10.3, 4.8 Hz, 1 H), 4.38 (d, J=12.5 Hz, 1 H), 4.68–4.75 (m, 2 H), 4.96 (dd, J=10.3, 4.0 Hz, 1 H), 5.24–5.29 (m, 2 H), 5.32 (d, J=4.0 Hz, 1 H), 5.64 (s, 1 H), 6.79 (dd, J=8.1, 1.5 Hz, 1 H), 7.31 (d, J=8.1 Hz, 1 H), 7.34–7.41 (m, 6 H), 7.82–7.86 (m, 2 H), 7.89–7.92 (m, 2 H), 9.44 IR (KBr) 3400, 2900, 1750, 1710, 1375, 1240 and 1050 cm$^{-1}$. mass spectrum (+FAB), m/z 909/911 (M+H). Anal. Calcd. for $C_{44}H_{45}N_2ClO_{17}$; C, 58.12; H, 4.99; N, 3.08. Found: C, 57.77; H, 4.85; N, 2.98.

EXAMPLE 7

N-(5-{[4',6'-O-Benzylidene-6-deoxy-6-(1,3-dioxo-1,3-dihydro-isoindol-2-yl)-β-D-maltosyl]-oxy-methyl}-2-chloro-phenyl)-acetamide

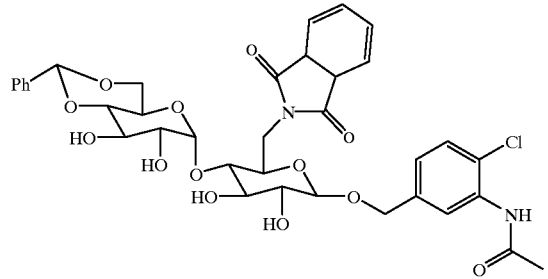

Using N-(5-{2,2',3,3'-tetra-O-acetyl-4',6'-O-benzylidene-6-deoxy-6-(1,3-dioxo-1,3-dihydro-isoindol-2-yl)-β-D-maltosyl]-oxy-methyl}-2-chloro-phenyl)-acetamide, the title compound was prepared according to the procedure of Example 3 to give 0.145 g (88%), white solid, mp 226–233° C.; $^1$H NMR (DMSO-d$_6$) δ2.07 (s, 3 H), 3.12–3.16 (m, 1 H), 3.39–3.47 (m, 4 H), 3.57–3.68 (m, 3 H), 3.81 (dd, J=14.2, 9.8 Hz, 1 H), 3.93–3.94 (m, 1 H), 4.04–4.07 (m, 1 H), 4.17 (d, J=7.9 Hz, 1 H), 4.22 (dd, J=9.8, 4.9 Hz, 1 H), 4.35 (ABq, J=12.0 Hz, Δδ=0.05, 2 H), 5.19 (d, J=4.0 Hz, 1 H), 5.27 (d, J=5.5 Hz, 1 H), 5.39 (d, J=5.1 Hz, 1 H), 5.58 (s, 1 H), 5.59 (d, J=2.0 Hz, 1 H), 5.84 (d, J=6.4 Hz, 1 H), 6.94 (dd, J=8.2, 2.0 Hz, 1 H), 7.30 (d, J=8.2 Hz, 1 H), 7.37–7.40 (m, 4 H), 7.45–7.48 (m, 2 H), 7.81–7.84 (m, 2 H), 7.88–7.90 (m, 2 H), 9.45 (s, 1 H). IR (KBr) 3400, 2900, 1710, 1400 and 1070 cm$^{-1}$. mass spectrum (+FAB), m/z 741/743 (M+H). Anal. Calcd. for $C_{36}H_{37}N_2ClO_{13}$ 0.75 H$_2$O: C, 57.30; H, 5.14; N, 3.71. Found: C, 57.37; H, 5.11; N, 3.58.

EXAMPLE 8

N-{5-[(6-Deoxy-6-O-azido-4',6'-O-benzylidene-3-D-maltosyl)-oxy-methyl]-2-chloro-phenyl}-acetamide step 1

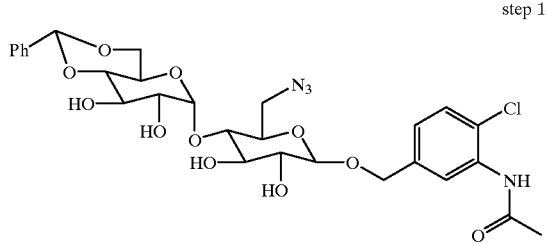

N-{5-[(2,2',3,3'-Tetra-O-acetyl-6-deoxy-6-azido-4',6'-O-benzylidene-β-D-maltosyl)-oxy-methyl]-2-chloro-phenyl}-acetamide A stirred solution containing N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.897 g, 0.960 mmol) and sodium azide (0.103 g, 1.58 mmol) in DMF (29 mL) was heated at 50° C. for 2 days. The reaction was cooled to room temperature, quenched with H$_2$O, extracted with EtOAc, dried (Na$_2$SO$_4$) and concentrated. Purification by flash chromatography (40 % acetone/hexane) gave 0.692 g (90%) of title compound as a solid; $^1$H NMR (DMSO-d$_6$) δ1.94 (s, 3 H), 1.96 (s, 3 H), 1.98 (s, 3 H), 2.00 (s, 3 H), 2.08 (s, 3 H), 3.57–3.88 (m, 4 H), 3.91–3.97 (m, 2 H) 4.02–4.05 (m, 1 H), 4.23 (dd, 1 H), 4.59 (d, J=12.7 Hz, 1 H), 4.71–4.78 (m, 2 H), 4.86–4.92 (m, 2 H), 5.22–5.36 (m, 3 H), 5.64 (s, 1 H), 7.08 (dd, J=8.3, 1.8 Hz, 1 H), 7.38 (s, 5 H), 7.47 (d, J=8.2 Hz, 1 H), 7.65 (s, 1 H), 9.53 (s, 1 H).

Step 2

N-{5-[(6-Deoxy-6-azido-4',6'-O-benzylidene-β-D-maltosyl)-oxy-methyl]-2-chloro-phenyl}-acetamide Using N-{5-[(2,2',3,3'-Tetra-O-acetyl-6-deoxy-6-azido-4',6'-O-benzylidene-β-D-maltosyl)-oxy-methyl]-2-chloro-phenyl}-acetamide, the title compound was prepared according to the procedure of Example 3 to give 0.127 g (82%), white solid, mp 203–204° C.; $^1$H NMR (DMSO-d$_6$) δ2.07 (s, 3 H), 3.10–3.16 (m, 1 H), 3.35–3.41 (m, 3 H), 3.45–3.58 (m, 4 H), 3.62–3.70 (m, 3 H), 4.09–4.15 (m, 1 H), 4.40 (d, J=7.7 Hz, 1 H), 4.67 (ABq, J=12.2 Hz, Δδ=0.09, 2 H), 5.13 (d, J=4.0 Hz, 1 H), 5.33 (d, J=5.1 Hz, 1 H), 5.36 (d, J=5.1 Hz, 1 H), 5.54 (d, J=3.3Hz, 1 H), 5.57 (s, 1 H), 5.68 (d, J=6.6 Hz 1 H), 7.19 (dd, J=8.3, 1.8 Hz, 1 H), 7.34–7.39 (m, 3 H), 7.42–7.46 (m, 3 H), 7.65 (s, 1 H), 9.52 (s, 1 H). IR (KBr)3400, 2850, 2100, 1700, 1300 and 1070 cm$^{-1}$. mass spectrum (+FAB) 637 (M+H). Anal. Calcd. for C$_{28}$H$_{33}$N$_4$ClO$_{11}$: C, 52.79; H, 5.22; N, 8.80. Found: C, 52.63; H, 5.05; N, 8.56.

What is claimed is:

1. A compound of formula I having the structure

I

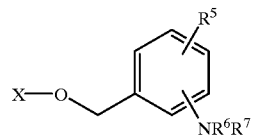

wherein X is

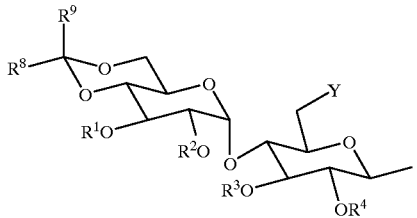

Y is hydrogen, halogen, azido, or Het optionally substituted with R$^{10}$;

Het is 1,3-dioxo-1,3-dihydro-isoindol-2-yl, imidazol-1-yl, or benzimidazol-1-yl;

R$^1$, R$^2$, R$^3$ and R$^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

R$^5$ is hydrogen, alkyl of 1–6 carbon atoms, perfluoroalkyl of 1–6 carbon atoms, halogen, nitrile, nitro, alkoxy of 1–6 carbon atoms;

R$^6$ and R$^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

R$^8$ and R$^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with R$^{11}$, aralkyl of 7–12 carbon atoms or aralkyl of 7–12 carbon atoms substituted with R$^{11}$;

R$^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

R$^{11}$ is halogen, nitrile, nitro, or perfluoroalkyl of 1–6 carbon atoms;

or a pharmaceutically acceptable salt thereof.

2. The compound according to claim 1, wherein
R$^1$, R$^2$, R$^3$ and R$^4$, are each, independently, hydrogen, or acyl of 2–7 carbon atoms;
R$^5$ is hydrogen, alkyl of 1–6 carbon atoms, or halogen;
R$^6$and R$^7$, are each, independently, hydrogen, or acyl of 2–7 carbon atoms;
R$^8$ and R$^9$, are each, independently, hydrogen, or aryl of 6–10 carbon atoms;
R$^{10}$ is halogen, nitrile, nitro, amino, acylamino of 2–7 carbon atoms, carboxyl, alkyl of 1–6 carbon atoms, alkoxy of 1–6 carbon atoms, or aryl of 6–10 carbon atoms;
or a pharmaceutically acceptable salt thereof.

3. The compound according to claim 2, wherein
R$^1$, R$^2$, R$^3$ and R$^4$, are each, independently, hydrogen, or acetyl;

$R^5$ is hydrogen, alkyl of 1–3 carbon atoms, or chloro;

$R^6$ is hydrogen;

$R^7$ is acetyl;

$R^8$ is phenyl;

$R^9$ is hydrogen;

$R^{10}$ is nitro;

or a pharmaceutically acceptable salt thereof.

4. The compound according to claim 1, which is N-(5-{[4',6'-O-Benzylidene-6-deoxy-6-(4-nitro-1H-imidazol-1-yl)-β-D-maltosyl-oxy]-methyl}-2-methyl-phenyl)-acetamide or a pharmaceutically acceptable salt thereof.

5. The compound according to claim 1, which is N-(5-{[2,3,2',3'-Tetra-O-acetyl-4',6'-O-benzylidene-6-deoxy-6-(4-nitro-1H-imidazol-1-yl)-β-D-maltosyl]-oxy-methyl}-2-chloro-phenyl)-acetamide or a pharmaceutically acceptable salt thereof.

6. The compound according to claim 1, which is N-(5-{[4',6'-O-Benzylidene-6-deoxy-6-(4-nitro-1H-imidazol-1-yl)-β-D-maltosyl]-oxy-methyl}-2-chloro-phenyl)-acetamide or a pharmaceutically acceptable salt thereof.

7. The compound according to claim 1, which is N-{5-[(2,2',3,3'-Tetra-O-acetyl-4',6',-O-benzylidene-6-deoxy-6-iodo-β-D-maltosyl)-oxy-methyl]-2-chloro-phenyl}-acetamide or a pharmaceutically acceptable salt thereof.

8. The compound according to claim 1, which is N-{5-[(4',6',-O-Benzylidene-6-deoxy-6-iodo-β-D-maltosyl)-oxy-methyl]-2-chloro-phenyl}-acetamide or a pharmaceutically acceptable salt thereof.

9. The compound according to claim 1, which is N-(5-{[2,2',3,3'-Tetra-O-acetyl-4',6'-O-benzylidene-6-deoxy-6-(1,3-dioxo-1,3-dihydro-isoindol-2-yl)-β-D-maltosyl]-oxy-methyl}-2-chloro-phenyl)-acetamide or a pharmaceutically acceptable salt thereof.

10. The compound according to claim 1, which is N-(5-{[4',6'-O-Benzylidene-6-deoxy-6-(1,3-dioxo-1,3-dihydro-isoindol-2-yl)-β-D-maltosyl]-oxy-methyl}-2-chloro-phenyl)-acetamide or a pharmaceutically acceptable salt thereof.

11. The compound according to claim 1, which is N-{5-[(6-Deoxy-6-O-azido-4',6'-O-benzylidene-β-D-maltosyl)-oxy-methyl]-2-chloro-phenyl}-acetamide or a pharmaceutically acceptable salt thereof.

12. A method of treating or inhibiting hyperproliferative vascular disorders in a mammal in need thereof, which comprises administering to said mammal an effective amount of a compound of formula I having the structure

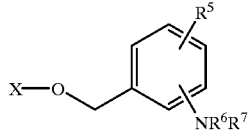

I wherein X is

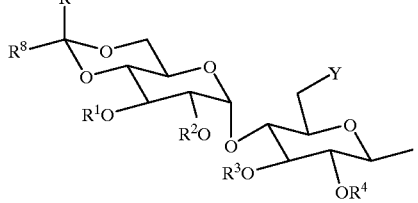

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl;

$R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

$R^{11}$ is halogen, nitrile, nitro, or perfluoroalkyl of 1–6 carbon atoms;

or a pharmaceutically acceptable salt thereof.

13. A method of treating or inhibiting restenosis in a mammal in need thereof, which comprises administering to said mammal an effective amount of a compound of formula I having the structure

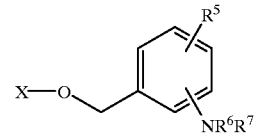

I wherein X is

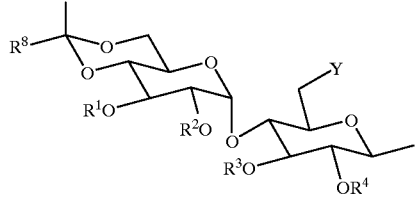

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl;

$R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

$R^{11}$ is halogen, nitrile, nitro, or perfluoroalkyl of 1–6 carbon atoms;

or a pharmaceutically acceptable salt thereof.

14. The method according to claim 13, wherein the restenosis results from a vascular angioplasty procedure, vascular reconstructive surgery, or organ or tissue transplantation.

15. A method of inhibiting angiogenesis in a malignant tumor, sarcoma, or neoplastic tissue in a mammal in need thereof, which comprises administering to said mammal an effective amount of a compound of formula I having the structure

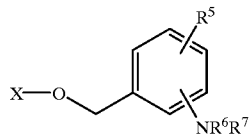

I wherein X is

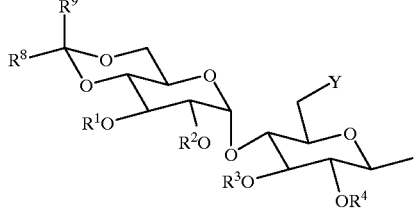

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl;

$R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

$R^{11}$ is halogen, nitrile, nitro, or perfluoroalkyl of 1–6 carbon atoms;

or a pharmaceutically acceptable salt thereof.

16. A pharmaceutical composition which comprises a compound of formula I having the structure

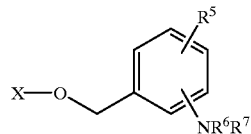

I wherein X is

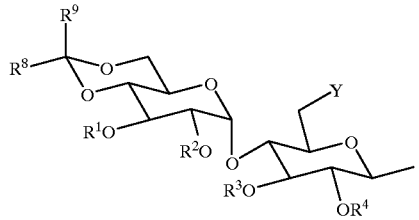

Y is hydrogen, halogen, azido, or Het optionally substituted with $R^{10}$;

Het is 1,3-dioxo-1,3-dihydro-isoindol-2-yl, imidazol-1-yl, or benzimidazol-1-yl;

$R^1$, $R^2$, $R^3$ and $R^4$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, benzoyl, or benzyl;

$R^5$ is hydrogen, alkyl of 1–6 carbon atoms, perfluoroalkyl of 1–6 carbon atoms, halogen, nitrile, nitro, alkoxy of 1–6 carbon atoms;

$R^6$ and $R^7$, are each, independently, hydrogen, acyl of 2–7 carbon atoms, perfluoroacyl of 2–7 carbon atoms, alkyl of 1–6 carbon atoms, perfluoroalkyl of 1–6 carbon atoms, alkylsulfonyl of 1–6 carbon atoms, perfluoroalkylsulfonyl of 1–6 carbon atoms, arylsulfonyl of 6–10 carbon atoms, or arylsulfonyl substituted with halo of 6–10 carbon atoms;

$R^8$ and $R^9$, are each, independently, hydrogen, alkyl of 1–6 carbon atoms, alkyl of 1–6 carbon atoms, haloalkyl of 1–6 carbon atoms, nitriloalkyl of 1–6 carbon atoms, nitroalkyl of 1–6 carbon atoms, alkoxy of 1–6 carbon atoms, aryl of 6–10 carbon atoms, aryl of 6–10 carbon atoms substituted with $R^{11}$, aralkyl of 7–12 carbon atoms or aralkyl of 7–12 carbon atoms substituted with $R^{11}$;

$R^{10}$ is halogen, nitrile, nitro, amino, acylamino of 2–7 carbon atoms, perfluoroacylamino of 2–7 carbon atoms, carboxyl, carboxyaldehyde, perfluoroalkyl of 1–6 carbon atoms, alkyl of 1–6 carbon atoms, alkoxy of 1–6 carbon atoms, perfluoroalkoxy of 1–6 carbon atoms, alkoxycarbonyl of 2–7 carbon atoms, perfluoroalkoxycarbonyl of 2–7 carbon atoms, aryl of 6–10 carbon atoms, or mercapto;

$R^{11}$ is halogen, nitrile, nitro, or perfluoroalkyl of 1–6 carbon atoms;

or a pharmaceutically acceptable salt thereof, and a pharmaceutical carrier.

* * * * *